(12) United States Patent
Baroni et al.

(10) Patent No.: US 8,153,637 B2
(45) Date of Patent: Apr. 10, 2012

(54) PHENYL-ALKYL PIPERAZINES HAVING TNF-MODULATING ACTIVITY, PREPARATION METHOD, AND THERAPEUTIC USE THEREOF

(75) Inventors: Marco Baroni, Paris (FR); Olaf Ritzeler, Frankfurt am Main (DE); Marco Zanchet, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/970,047

(22) Filed: Dec. 16, 2010

(65) Prior Publication Data

US 2011/0144120 A1      Jun. 16, 2011

Related U.S. Application Data

(63) Continuation of application No. PCT/FR2009/051138, filed on Jun. 16, 2009.

(30) Foreign Application Priority Data

Jun. 16, 2008  (FR) ..................................... 08 03337
Dec. 23, 2008  (FR) ..................................... 08 07361

(51) Int. Cl.
  *A61K 31/495* (2006.01)
  *A61K 31/496* (2006.01)
  *C07D 213/74* (2006.01)
  *C07D 295/096* (2006.01)
  *C07D 295/04* (2006.01)

(52) U.S. Cl. .............. 514/253.01; 514/255.03; 544/360; 544/392; 544/394

(58) Field of Classification Search ........................ None
See application file for complete search history.

(56) References Cited

U.S. PATENT DOCUMENTS 3,732,229 A  *  5/1973  Bysouth et al. ............... 544/394

FOREIGN PATENT DOCUMENTS

| FR | 2932480 | * | 8/2008 |
| JP | 2001072660 | | 3/2001 |
| WO | WO 2004/060308 | | 7/2004 |

OTHER PUBLICATIONS

Hanano, T., et al., Novel Phenylpiperazine Derivatives as Dual Cytokine Regulators with TNF-a Suppressing and IL-10 Augmenting Activity, Bioorganic & Medicinal Chemistry Letter, vol. 10, (2000), pp. 875-879.

Hanano, T., et al., Novel DMARDs on the Basis of a New Concept of Dual Cytokine Regulation, TNF-a Suppression and IL-10 Augmentation, Bioorganic & Medicinal Chemistry Letters, vol. 10, pp. 881-884, (2000).

Potter, G. A., et al., Highly Stereoselective Access to an (E)-Vinyl Bromide From an Aryl Ketone Leads to Short Synthesis of (Z)-Tamoxifen and Important Substituted Derivatives, J. Org. Chem., vol. 55, pp. 6184-6187, (1990).

Black, R. A., et al., Agents that Block TNF-a Synthesis or Activity, Annual Reports in Medicinal Chemistry, vol. 32, pp. 241-250, (1997).

* cited by examiner

*Primary Examiner* — Emily Bernhardt
(74) *Attorney, Agent, or Firm* — Ronald G. Ort

(57) ABSTRACT

The present invention relates to phenyl-alkyl piperazines of formula (I):

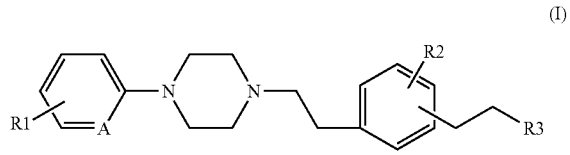

in which A, R1, R2 and R3 are as defined herein, having TNF-modulating activity. The invention also relates to the preparation thereof, pharmaceutical compositions thereof, and to the therapeutic use thereof.

13 Claims, No Drawings

PHENYL-ALKYL PIPERAZINES HAVING TNF-MODULATING ACTIVITY, PREPARATION METHOD, AND THERAPEUTIC USE THEREOF

The present invention relates to novel phenyl-alkyl piperazines with TNF-modulating activity, to pharmaceutical compositions containing them and to a process for preparing them.

TNF-alpha is a cytokine that has been identified as a mediator of immunity, of inflammation, of cell proliferation, of fibrosis, etc. This mediator is present in large quantities in inflamed synovial tissues and plays an important role in the pathogenesis of autoimmunity (*Annu. Rep. Med. Chem.*, 1997, 32:241-250).

It has now been found that phenyl-alkyl piperazines have strong activity towards the modulation of TNF-alpha, more particularly inhibiting activity.

Thus, according to one of its aspects, the present invention relates to phenyl-alkyl-piperazines of formula (I):

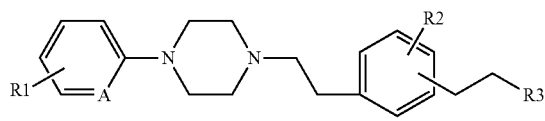

in which:
  R1 and R2 represent, independently of each other, a hydrogen atom, a halogen atom, a (C1-C5)alkyl group, a (C1-C5)haloalkyl group, a (C1-C2)perfluoroalkyl group, a (C1-C5)alkoxy group or a (C1-C2)perfluoroalkoxy group;
  R3 represents a (C1-C5)alkyl group;
  A represents =CH— or =N—.

The compounds of formula (I) may include one or more asymmetric carbon atoms. They may thus exist in the form of enantiomers or diastereoisomers. These enantiomers and diastereoisomers, and mixtures thereof, including racemic mixtures, form part of the invention.

The compounds of formula (I) may exist in the form of bases or acid-addition salts. Such addition salts form part of the invention.

These salts may be prepared with pharmaceutically acceptable acids; however the salts with other acids that are useful, for example, for the purification or isolation of the compounds of formula (I), also form part of the invention.

The compounds of formula (I) may exist as N-oxide derivatives. Indeed, the compounds of formula (I) may especially bear one or two N-oxide groups on the piperazine. Although, in principle, the two abovementioned nitrogens can both be oxidized, the compounds bearing only one N-oxide are preferred.

According to another subject of the invention, mention may be made of the compounds of formula (I) in which:
  R1 represents a (C1-C5)haloalkyl group, more particularly a (C1-C5)fluoroalkyl group, a (C1-C2)perfluoroalkyl group; and/or
  R2 represents a hydrogen atom or a (C1-C5)alkyl group; in the form of the base or an acid-addition salt.

According to another subject of the invention, the piperazine is linked via the ethyl group in position 3 on the phenyl group:

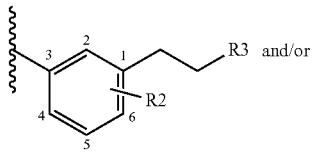

R1 represents a (C1-C2)perfluoroalkyl group; and/or
  R2 represents a hydrogen atom or a (C1-C3)alkyl group.

According to another subject of the invention, mention may be made of the following compounds of formula (I):
  1-(3-trifluoromethylphenyl)-4-[2-(4-methyl-3-pentylphenyl)ethyl]piperazine;
  in the form of the base or an acid-addition salt.

According to another subject of the invention, mention may be made of a compound of formula (I) chosen from:
  compound 1: 1-(3-trifluoromethylphenyl)-4-[2-(4-methyl-3-pentylphenyl)ethyl]piperazine hemipamoate;
  compound 1 bis: 1-(3-trifluoromethylphenyl)-4-[2-(4-methyl-3-pentyl-phenyl)ethyl]piperazine hemipamoate as a mixture with 0.5 mol of free pamoic acid;
  compound 2: 1-(3-trifluoromethylphenyl)-4-[2-(4-methoxy-3-pentyl-phenyl)ethyl]piperazine hydrochloride;
  compound 3: 1-(3-trifluoromethylphenyl)-4-[2-(4-methyl-3-propylphenyl)-ethyl]piperazine hydrochloride;
  compound 4: 1-(3-fluorophenyl)-4-[2-(4-methyl-3-pentylphenyl)ethyl]-piperazine hydrochloride;
  compound 5: 1-(3-trifluoromethylphenyl)-4-[2-(4-methyl-3-heptylphenyl)-ethyl]piperazine hydrochloride;
  compound 6: 1-(6-trifluoromethylpyrid-2-yl)-4-[2-(4-methyl-3-pentyl-phenyl)ethyl]piperazine hydrochloride;
  compound 7: 1-(3-fluorophenyl)-4-[2-(4-methoxy-3-pentylphenyl)ethyl]-piperazine hydrochloride;
  compound 8: 1-(3-difluoromethylphenyl)-4-[2-(4-methyl-3-pentylphenyl)-ethyl]piperazine hydrochloride;
  compound 9: 1-(phenyl)-4-[2-(4-methyl-3-pentylphenyl)ethyl]piperazine hydrochloride;
  compound 10:1-(3-methoxyphenyl)-4-[2-(4-methyl-3-pentylphenyl)-ethyl]piperazine hydrochloride;
  compound 11: 1-(3-trifluoromethylphenyl)-4-[2-(4-methyl-3-(2-methylbutyl)phenyl)ethyl]piperazine hydrochloride;
  compound 12: 1-(3-difluoromethylphenyl)-4-[2-(4-methoxy-3-pentyl-phenyl)ethyl]piperazine hydrochloride;
  compound 13: 1-(3-trifluoromethylphenyl)-4-[2-(4-methoxy-3-heptyl-phenyl)ethyl]piperazine hydrochloride;
  compound 14: 1-(3-trifluoromethylphenyl)-4-[2-(4-methyl-3-hexylphenyl)-ethyl]piperazine hydrochloride;
  compound 15: 1-(3-trifluoromethylphenyl)-4-[2-(4-methoxy-3-propyl-phenyl)ethyl]piperazine hydrochloride;
  compound 16: 1-(phenyl)-4-[2-(4-methoxy-3-pentylphenyl)ethyl]piper-azine hydrochloride;
  compound 17: 1-(4-chlorophenyl)-4-[2-(4-methyl-3-pentylphenyl)ethyl]-piperazine hydrochloride;
  compound 18: 1-(3-trifluoromethylphenyl)-4-[2-(4-methyl-3-pentyl-phenyl)ethyl]piperazine hydrochloride;
  compound 19: 1-(3-trifluoromethylphenyl)-4-[2-(4-methyl-3-pentyl-phenyl)ethyl]piperazine benzenesulfonate;
  compound 20: 1-(3-trifluoromethylphenyl)-4-[2-(4-methyl-3-pentyl-phenyl)ethyl]piperazine 2-naphthalenesulfonate;
  compound 21: 1-(3-trifluoromethylphenyl)-4-[2-(4-methyl-3-pentyl-phenyl)ethyl]piperazine p-tolylsulfonate;

compound 22: 1-(3-trifluoromethylphenyl)-4-[2-(4-methyl-3-pentyl-phenyl)ethyl]piperazine hemi-2,5-naphthalene-disulfonate;
compound 23: 1-(4-fluorophenyl)-4-[2-(4-methyl-3-pentylphenyl)ethyl]-piperazine dihydrochloride;
compound 24: 1-(4-methoxyphenyl)-4-[2-(4-methyl-3-pentylphenyl)-ethyl]piperazine (base);
compound 25: 1-(5-bromopyrid-2-yl)-4-[2-(4-methyl-3-pentylphenyl)-ethyl]piperazine dihydrochloride;
compound 26: 1-[2-(4-methyl-3-pentylphenyl)ethyl]-4-(5-trifluoromethylpyrid-2-yl)piperazine dihydrochloride;
compound 27: 1-(4-tert-butylphenyl)-4-[2-(4-methyl-3-pentylphenyl)-ethyl]piperazine hydrochloride;
compound 28: 1-(4-ethoxyphenyl)-4-[2-(4-methyl-3-pentylphenyl)ethyl]-piperazine dihydrochloride;
compound 29: 1-[2-(4-methyl-3-pentylphenyl)ethyl]-4-m-tolylpiperazine dihydrochloride;
compound 30: 1-[2-(4-methyl-3-pentylphenyl)ethyl]-4-pyrid-2-ylpiperazine dihydrochloride;
compound 31: 1-(6-bromopyrid-2-yl)-4-[2-(4-methyl-3-pentylphenyl)-ethyl]piperazine hydrochloride;
compound 32: 1-(2-chlorophenyl)-4-[2-(4-methyl-3-pentylphenyl)ethyl]-piperazine hydrochloride;
compound 33: 1-(2-methylphenyl)-4-[2-(4-methyl-3-pentylphenyl)ethyl]-piperazine hydrochloride;
compound 34: 1-(3-trifluoromethoxyphenyl)-4-[2-(4-methyl-3-pentyl-phenyl)ethyl]piperazine hydrochloride;
compound 35: 1-(5-chloropyrid-2-yl)-4-[2-(4-methyl-3-pentylphenyl)-ethyl]piperazine hydrochloride;
compound 36: 1-(3-trifluoromethylphenyl)-4-[2-(4-methyl-3-pentyl-phenyl)ethyl]piperazine oxalate;
compound 37: 1-(3-trifluoromethylphenyl)-4-[2-(4-methyl-3-pentyl-phenyl)ethyl]piperazine fumarate;
compound 38: 1-(3-trifluoromethylphenyl)-4-[2-(4-methyl-3-pentyl-phenyl)ethyl]piperazine succinate;
compound 39: 1-(3-trifluoromethylphenyl)-4-[2-(4-methyl-3-pentyl-phenyl)ethyl]piperazine dihippurate.

In the context of the present invention, the following definitions apply:

"a halogen atom" means fluorine, chlorine, bromine or iodine;

"an alkyl group" means a linear or branched saturated aliphatic group. For example, a (C1-C5)alkyl group comprises 1 to 5 carbon atoms. Examples that may be mentioned more particularly include methyl, ethyl, propyl, isopropyl, butyl, isobutyl, tert-butyl, pentyl, isopentyl, etc. groups.

"a haloalkyl group" means an alkyl group as defined hereinabove in which one or more hydrogen atoms have been replaced with a halogen atom: for example a fluoroalkyl group may comprise one or more fluorine atoms;

"a perfluoroalkyl group" means an alkyl group as defined hereinabove in which all the hydrogen atoms have been replaced with a fluorine atom;

"an alkoxy group" means an —O-alkyl group in which the alkyl is as defined hereinabove;

"a perfluoroalkoxy group" means an alkoxy group in which all the hydrogen atoms have been replaced with a fluorine atom.

The term "leaving group" means hereinbelow a group that can be readily cleaved from a molecule by breaking a heterolytic bond, with the loss of an electron pair. This group may thus be readily replaced with another group during a substitution reaction, for example. Such leaving groups are, for example, halogens or an activated hydroxyl group such as methanesulfonate, benzenesulfonate, p-toluenesulfonate, triflate, acetate, etc. Examples of leaving groups, and also references regarding their preparation, can be found in Advances in Organic Chemistry, J. March, 3rd Edition, Wiley Interscience, pp. 310-316.

The compounds of formula (I) may be prepared according to Scheme 1:

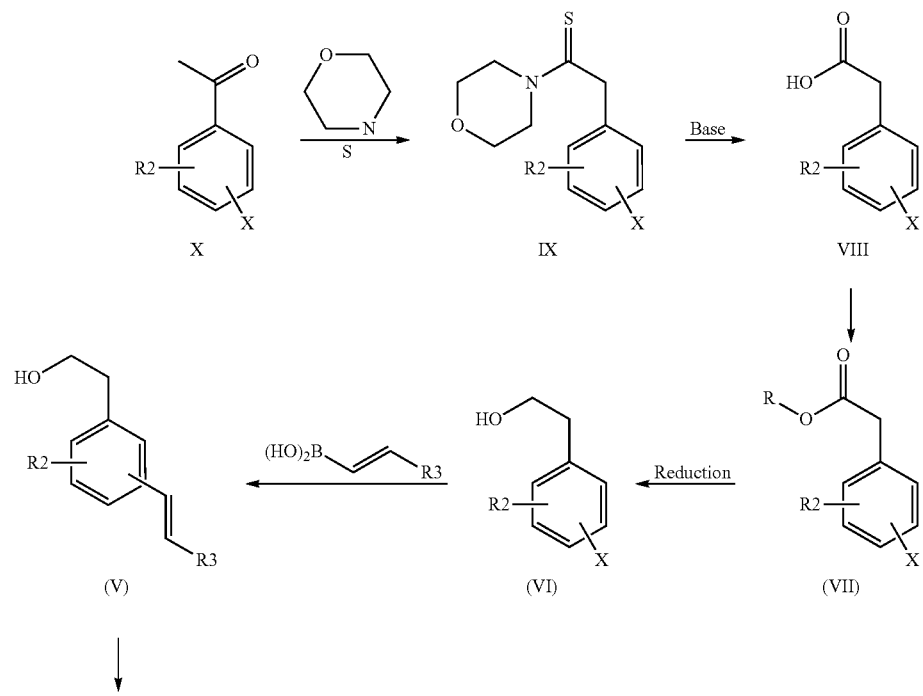

-continued

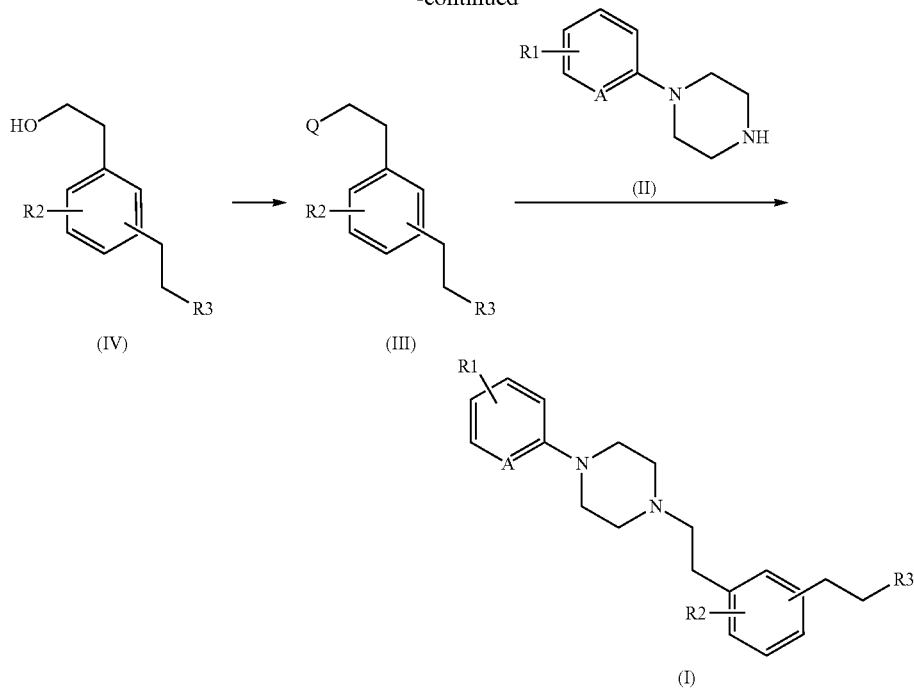

According to this scheme, the compounds of formula (I) can be synthesized by condensation of a compound of formula (II)

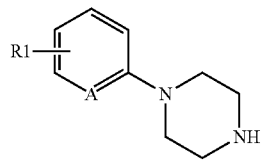

in which R1 and A are as defined hereinabove, with a compound of formula (III)

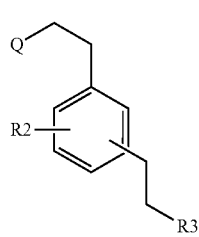

in which R2 and R3 are as defined above and Q is a leaving group.

Examples of leaving groups Q that may be used include a halogen atom or any group capable of condensing with an amine. The condensation reaction is performed in a conventional manner by mixing the starting compounds (II) and (III) in an organic solvent such as an alcohol, for example methanol or butanol, optionally in the presence of a base such as an alkali metal carbonate, 4-dimethylaminopyridine or triethylamine, at a temperature of between room temperature and the reflux point of the chosen solvent. "Room temperature" means a temperature between 5 and 25° C.

The compound of formula (III) is prepared by conversion of the hydroxyl of the compound of formula (IV) into a leaving group Q according to conventional methods known to those skilled in the art. For example, the hydroxyl can be converted into a halogen such as bromine in the presence of bromic acid, carbon tetrabromide or thionyl bromide; or alternatively such as a chlorine in the presence of thionyl chloride. The mesyloxy ($CH_3$—$SO_2$—O—) or tosyloxy (tolyl-$SO_2$—O) groups can thus be prepared as leaving groups by reacting the products of formula (IV) with methanesulfonyl or p-tolylsulfonyl chloride.

Compound (IV) is obtained by reduction of the double bond of the compound of formula (V). The reduction can be performed according to conventional methods known to those skilled in the art, for example in the presence of hydrogen with palladium/charcoal catalysis in an organic solvent such as ethanol at a temperature of between 20 and 40° C.

The compound of formula (V) can be prepared via the Suzuki reaction (J. Org. Chem., 55 6184-1990). According to this method, a compound of formula (VI) in which X represents a halogen, more particularly bromine or iodine; or a trifluoromethylsulfonate, is reacted with a vinylboronic acid or a vinylboronate in the presence of a catalyst such as palladium acetate or tetrakis(triphenylphosphine)palladium in a solvent such as tetrahydrofuran, dioxane or dimethoxyethane.

The compound of formula (VI) can be obtained from the compound of formula (X) according to the steps described in Scheme 1 under conditions well known to those skilled in the art and the like, or as detailed in the examples.

The compounds of formula (II) are commercially available or may be prepared according to methods well known to those skilled in the art.

In the scheme, the starting compounds and the reagents, when their preparation method is not described, are commercially available or are described in the literature, or alternatively may be prepared according to methods described therein or that are known to those skilled in the art.

The process according to the invention may also comprise the step of isolation and/or purification of the compound of formula (I) thus obtained and/or its optional conversion into a salt thereof and/or its N-oxide.

The desired compound is isolated according to conventional techniques in the form of the free base or of a salt thereof. The free base may be converted into a salt thereof by simple salification in an organic solvent such as an alcohol, preferably ethanol or isopropanol, an ether such as 1,2-dimethoxyethane, ethyl acetate, acetone or a hydrocarbon such as hexane.

The compounds of formula (I) bearing an N-oxide group on the nitrogen atoms can be prepared by oxidation of the corresponding compounds of formula (I). In this case, the compound of formula (I) as obtained via the above syntheses is subjected to an oxidation reaction according to conventional methods, for example to a reaction with m-chloroperbenzoic acid in a suitable solvent, and isolated according to the usual techniques well known to those skilled in the art.

The following examples describe the preparation of a compound according to the invention. These examples are not limiting and serve merely to illustrate the present invention. The number of the compound presented in example refers to that given in the table below, which illustrates the chemical structure and the physical properties of the compound according to the invention.

The physicochemical measurements were performed as follows:

The melting points were measured with a Büchi B540 machine.

The proton nuclear magnetic resonance spectra ($^1$H NMR) were recorded at 500 MHz on a Brüker machine equipped with an Avance console. The chemical shifts are reported in ppm relative to the TMS frequency.

All the spectra were recorded at a temperature of 40° C.

The abbreviations used to characterize the signals are as follows: s=singlet, bs=broad singlet, m=multiplet, bm=broad multiplet, d=doublet, t=triplet, q=quartet.

•=not integrable owing to interference with a broad peak from water.

For the LC/MS technique:

ThermoElectron LCQ Deca XP Max System equipped with both an ion trap mass spectrometry detector and a diode array detector.

The chromatographic systems used are as follows:

Method A)
Kromasil C18 column (2.1×50 mm) 3.5 μm
Eluent A=H$_2$O ammonium acetate 5 mM pH 6.5
Eluent B=CH$_3$CN.
Gradient from 98% A to 95% B over 12 minutes, then elution at 95% B over 3 minutes
Flow rate 0.5 ml/minute
Injection of 2 μL of a 0.1 mg/ml solution in a 9/1 CH$_3$CN/H$_2$O mixture Method B)
Kromasil C18 column (2.1×50 mm) 3.5 μm
Eluent A=H$_2$O+0.01% TFA
Eluent B=CH$_3$CN.
Gradient from 98% A to 95% B over 15 minutes, then elution at 95% B over 5 minutes
Flow rate 0.5 ml/minute
Injection of 2 μL of a 0.1 mg/ml solution in a 9/1 CH$_3$CN/H$_2$O mixture Method C)
Varian Sunfire C18 column (2.0×100 mm) 3.5 μm
Eluent A=H$_2$O+0.01% TFA
Eluent B=CH$_3$CN.
Gradient from 98% A to 95% B over 15 minutes, then elution at 95% B over 5 minutes
Flow rate 0.5 ml/minute
Injection of 2 μL of a 0.1 mg/ml solution in a 9/1 CH$_3$CN/H$_2$O mixture Method D)
Waters Atlantis DB C18 column (2.0×50 mm) 3.0 μm
Eluent A=H$_2$O+0.01% TFA
Eluent B=CH$_3$CN.
Gradient from 98% A to 95% B over 15 minutes, then elution at 95% B over 5 minutes
Flow rate 0.5 ml/minute
Injection of 2 μL of a 0.1 mg/ml solution in a 9/1 CH$_3$CN/H$_2$O mixture Method E)
XTerra C18 column (2.1×50 mm) 3.5 μm No. 186000400
Eluent A=H$_2$O+0.01% TFA
Eluent B=CH$_3$CN.
Gradient from 98% A to 95% B over 15 minutes, then elution at 98% B over 5 minutes.
Flow rate 0.5 ml/minute
Injection of 2 μL of a 0.1 solution in a 9/1 CH$_3$CN/H$_2$O mixture Method F)
Ascentis C18 column 2×50 mm 3 μm
Eluent A=H$_2$O+0.01% TFA
Eluent B=CH$_3$CN
Gradient from 98% A to 95% B over 10 minutes, then elution at 95% B over 5 minutes.
Flow rate 0.5 ml/minute; temperature 40° C.
Injection of 2 μL of a 0.1 mg/ml solution in a 9/1 CH$_3$CN/H$_2$O mixture Method G)
Ascentis C18 column 2×50 mm 3 μm
Eluent A=H$_2$O+0.05% TFA
Eluent B=CH$_3$CN+0.035 ml TFA
Gradient from 98% A to 95% B over 12 minutes, then elution at 95% B over 3 minutes.
Flow rate 0.7 ml/minute; temperature 40° C.
Injection of 2 μL of a 0.1 mg/ml solution in a 9/1 CH$_3$CN/H$_2$O mixture The products are detected by UV at 220 nm.
For the mass spectrometry section:
Ionization mode: positive electrospray (ESI+polarity+)
Scanning from 100 to 1200 amu
The silica gel for the flash column chromatography is sold by Biotage.

PREPARATION 1

4-(2-Bromoethyl)-1-methyl-2-pentylbenzene 1a) (3-Bromo-4-methylphenyl)acetic acid 13 g (0.061 mol) of 3-bromo-4-methylacetophenone, 2.1 g (0.065 mol) of sulfur, 14 ml of morpholine and a catalytic amount of p-toluenesulfonic acid monohydrate are mixed together. The mixture is heated under a stream of nitrogen at 130° C. After 7 hours, the mixture is cooled, 35 ml of absolute ethanol are added and the mixture is stirred at room temperature overnight. 13.9 g of the thioamide thus formed are dissolved in a solution of 110 ml of ethanol, 70 ml of water and 6 g of NaOH, and the mixture is refluxed for 4 hours. The solvents are evaporated off and the mixture is then acidified with dilute hydrochloric acid solution. A white solid precipitates. The precipitate is filtered off and 9.16 g of the title compound are obtained.

1b) 2-(3-Bromo-4-methylphenyl)ethanol

The compound of preparation 1a) is dissolved in 170 ml of ethanol. Gaseous hydrogen chloride is bubbled into the mixture for 30 minutes. The mixture is refluxed for 3 hours. The ethanol is evaporated off and the residue is taken up in diethyl ether. The mixture is washed with saturated sodium bicarbonate solution and evaporated under vacuum. 7.1 g of ester are obtained, and are dissolved in 70 ml of THF. A solution of 7.6 ml of borane/dimethyl sulfide in 110 ml of THF is added dropwise, under nitrogen, and the resulting mixture is refluxed for 3 hours. This mixture is cooled to 0° C. and 120 ml of methanol are added cautiously. The mixture is refluxed for 30 minutes and evaporated under vacuum. The residue is dissolved in ethyl acetate, washed with dilute aqueous ammonia solution, dried and evaporated under vacuum.

5.4 g of an oil corresponding to the title compound are obtained.

1c) 2-[4-methyl-3-(pent-1-enyl)phenyl]ethanol 2.0 g (0.0093 mol) of the product obtained in the previous step, 1.12 g (0.01 mol) of pentenylboronic acid, 2.1 g (0.037 mol) of KOH, 1.5 g (0.0046 mol) of tetrabutylammonium bromide and 50 mg of tetrakis(triphenylphosphine)palladium are mixed together in 50 ml of THF. The mixture is refluxed under a stream of nitrogen for 4 hours. The mixture is poured into water and extracted with diethyl ether, the organic phase is dried and the solvent is evaporated off. The residue is purified by column chromatography on silica gel, eluting with a 9/1 hexane/ethyl acetate mixture. 740 mg of the title product are obtained in the form of an oil.

1d) 2-(4-methyl-3-pentylphenyl)ethanol

The product obtained in the previous step, 0.74 g (0.0036 mol), is dissolved in 46 ml of ethanol, 0.12 g of 10% Pd/C is added and the mixture is left to react under a stream of hydrogen for 5 hours at a temperature of 40° C. The reaction mixture is filtered and evaporated under vacuum. 0.65 g of the title compound is obtained in the form of an oil.

1e) 4-(2-Bromoethyl)-1-methyl-2-pentylbenzene

The product obtained in the previous step, 0.65 g (0.0032 mol), is placed in a round-bottom flask with 8 ml of aqueous 48% hydrobromic acid solution. The mixture is heated at 130° C. for 6 hours, cooled and poured into saturated sodium bicarbonate solution. The resulting mixture is extracted with ethyl acetate, dried and evaporated under vacuum. 0.65 g of the title compound is obtained in the form of an oil.

PREPARATION 2

4-(2-Methanesulfonyloxyethyl)-1-methoxy-2-pentylbenzene

2a) (3-Bromo-4-methoxyphenyl)acetic acid

By working as described for preparation 1a), but using 3-bromo-4-methoxy-acetophenone instead of 3-bromo-4-methylacetophenone, the title compound is obtained.

2b) 2-(3-Bromo-4-methoxyphenyl)ethanol

By working as described for preparation 1b), but using compound 2a) from the previous step instead of compound 1a), the title compound is obtained.

2c) 2-[4-methoxyl-3-(pent-1-enyl)phenyl]ethanol

By working as described for preparation 1c), but using compound 2b) from the previous step instead of compound 1b), the title compound is obtained.

2d) 2-(4-methoxy-3-pentylphenyl)ethanol

By working as described for preparation 1d), but using compound 2c) from the previous step instead of compound 1c), the title compound is obtained.

2e) 4-(2-Methanesulfonyloxyethyl)-1-methoxy-2-pentylbenzene 1.2 g (0.0054 mol) of the compound 2d) from the previous step, 20 ml of dichloromethane, 0.75 ml (0.0054 mol) of triethylamine and, at 0-5° C., 0.42 ml (0.0054 mol) of methanesulfonyl chloride are placed in a round-bottom flask.

The mixture is stirred for 2 hours at room temperature, washed with water and dried, and the organic phase is evaporated under vacuum. The title product is obtained in the form of a yellow oil.

EXAMPLE 1

Compound 1: 1-[2-(4-methyl-3-pentylphenyl)ethyl]-4-(3-trifluoromethylphenyl)piperazine and its hemipamoate 1.98 g (0.00777 mol) of the compound of preparation 1, 1.5 g (0.0065 mol) of (3-trifluoromethylphenyl)-1-piperazine, 1.35 g (0.00975 mol) of potassium carbonate and 40 ml of n-butanol are placed in a round-bottom flask. The mixture is refluxed for 6 hours. The n-butanol is evaporated off, the residue is taken up in ethyl acetate and washed with water, the organic phase is dried and the solvent is evaporated off. The residue is purified by column chromatography on silica gel eluting with a 95/5 hexane/ethyl acetate mixture.

A solution of 300 mg of the free base obtained in THF is mixed with a solution of 180 mg of pamoic acid in 8/2 THF/water.

The reaction mixture is concentrated under vacuum, 6 ml of ethanol are added and a solid is obtained, which is then filtered off. The solid is crystallized by heating with ethanol and the off-white hemipamoate is obtained: 450 mg, m.p.=156-157. A further crystallization in ethanol affords an m.p. of 157-158.

Melting point=157-158° C.;

M+H$^+$ (method A)=RT 10.9 min m/z 419 (MH$^+$)

$^1$H NMR: δ (ppm, DMSO-d6): 0.88 (m; 3H); 1.27-1.39 (m; 4H); 1.45-1.59 (m; 2H); 2.23 (s; 3H); 2.50-2.58 (m; 2H**); 2.75-2.89 (m; 2H); 2.89-3.50 (m; 10H*); 4.74 (s; 1H); 6.97 (dd; Ja=7.7 Hz; Jb=1.4 Hz; 1H); 7.02 (d; J=1.4 Hz; 1H); 7.07 (d; J=7.7 Hz; 1H); 7.08-7.15 (m; 2H); 7.16-7.32 (m; 3H); 7.45 (dd→t; J=8 Hz; 1H); 7.74 (d; J=8 Hz; 1H); 8.17 (d; J=8 Hz; 1H); 8.30 (s; 1H).

According to one of the variants of the present invention, compound 1 bis is prepared, which is a mixture of 1-[2-(4-methyl-3-pentylphenyl)ethyl]-4-(3-trifluoromethylphenyl)piperazine hemipamoate and free pamoic acid (mol ratio 1:0.5), according to the following method:

600 mg of the free base obtained according to the method of Example 1 as a solution in THF are mixed with 540 mg of pamoic acid as an 8/2 THF/water solution. The mixture is evaporated under vacuum, and the residue is then treated with a mixture of THF and isopropyl ether, heated and filtered. 1 g of a yellow solid is obtained.

Melting point=158-159° C.;
M+H$^+$ (method B)=RT 10.1 min m/z 419 (MH$^+$)

EXAMPLE 2

Compound 2: 1-[2-(4-methoxy-3-pentylphenyl)ethyl]-4-(3-trifluoromethylphenyl)piperazine and its hydrochloride 0.336 g (0.00112 mol) of the compound of preparation 2, 20 ml of isopropanol, 0.47 ml of triethylamine (0.0036 mol), and 0.21 ml (0.00112 mol) of 4-(3-trifluoromethylphenyl)piperazine are placed in a round-bottom flask. The mixture is heated at the reflux temperature overnight. The solvent is evaporated off under vacuum, and an oil is obtained and purified by chromatography, eluting with an 8/2 hexane/ethyl acetate mixture. 300 mg of free base are obtained, from which the hydrochloride is prepared in isopropanol using an isopropanol solution saturated with HCl.

After filtration, 100 mg of a white solid are obtained.
Melting point=146-149° C.
M+H$^+$ (method B)=RT 7.0 min m/z 435 (MH$^+$)

$^1$H NMR: δ (ppm, DMSO-d6): 0.88 (m; 3H); 1.23-1.38 (m; 4H); 1.53 (m; 2H); 2.51-2.57 (m; 2H**); 2.95-3.05 (m; 2H); 3.11-3.28 (m; 4H); 3.30-3.41 (m; 2H); 3.60-3.70 (m; 2H*); 3.77 (s; 3H); 3.93-4.04 (m; 2H); 6.92 (d; J=8 Hz; 1H); 7.05 (d; J=2 Hz; 1H); 7.07 (dd; Ja=8 Hz; Jb=2 Hz; 1H); 7.17 (bd; J=7 Hz; 1H); 7.29 (bs; 1H); 7.31 (bd; J=8 Hz; 1H); 7.49 (dd->t; J=8 Hz; 1H); 10.59 (bs; 1H).

EXAMPLE 3

Compound 38: 1-[2-(4-methyl-3-pentylphenyl)ethyl]-4-(3-trifluoromethylphenyl)piperazine and its oxalate 0.24 g (0.89 mmol) of the compound of preparation 1, 0.24 g (0.1 mmol) of (3-trifluoromethylphenyl)-1-piperazine, 0.22 g (1.6 mmol) of potassium carbonate and 10 ml of n-butanol are placed in a round-bottom flask. The mixture is refluxed for 6 hours. The n-butanol is evaporated off, the residue is taken up in ethyl acetate and washed with water, the organic phase is dried and the solvent is evaporated off. The residue is purified by column chromatography on silica gel, eluting with a 95/5 hexane/ethyl acetate mixture. 130 mg of the title product are thus obtained in the form of an oil. The product is dissolved in 2 ml of isopropanol. A solution of oxalic acid in isopropanol is added to precipitate the oxalate which is then isolated by filtration in the form of a white solid (0.12 g).

Melting point=193-194° C.;
M+H$^+$=RT 6.7 min m/z 419 (MH$^+$)

$^1$H NMR δ (ppm, DMSO-d6): 0.89 (m; 3H); 1.28-1.40 (m; 4H); 1.46-1.59 (m; 2H); 2.23 (s; 3H); 2.50-2.57 (m;**); 2.78-2.89 (m; 2H); 2.91-3.08 (m;*); 3.39 (bs; 4H); 6.97 (dd; Ja=7.7 Hz; Jb=1.6 Hz; 1H); 7.02 (bs; 1H); 7.07 (d; J=7.7 Hz; 1H); 7.12 (d; J=7.4 Hz; 1H); 7.22 (bs; 1H); 7.27 (bd; J=8.4 Hz; 1H); 7.45 (m; 1H).

TABLE

| No. | R1 | R2 | R3 | Salt | m.p. °C. | M + H+ |
|---|---|---|---|---|---|---|
| 1 | 3-CF$_3$-phenyl | 4-CH$_3$ | 3-n-C$_3$H$_7$ | pamoate (0.5) | 157-158° C. | MH+ 419 RT 10.9 method A |

TABLE-continued

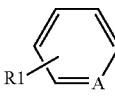

| No. | R1 / A | R2 | R3 | Salt | m.p. °C. | M + H+ |
|---|---|---|---|---|---|---|
| 1 bis | 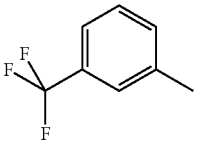 | 4-CH₃ | 3-n-C₃H₇ | 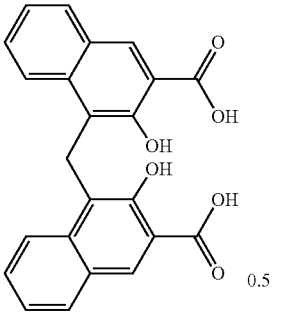<br>+ 0.5 mol free pamoic acid | 158-159° C. | MH+ 419<br>RT 10.1<br>method B |
| 2 | 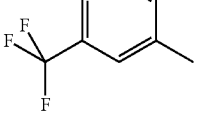 | 4-OCH₃ | 3-n-C₃H₇ | HCl | 146-149° C. | MH+ 435<br>RT 7.0<br>method B |
| 3 | 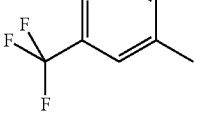 | 4-CH₃ | 3-CH₃ | HCl | 198-200° C. | MH+ 391<br>RT. 6.6<br>method B |
| 4 | 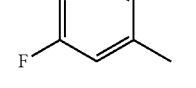 | 4-CH₃ | 3-n-C₃H₇ | HCl | 215-217° C. | MH+ 369<br>RT 7.4<br>method B |
| 5 | 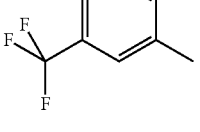 | 4-CH₃ | 3-n-C₅H₁₁ | HCl | 190-192° C. | MH+ 447<br>RT 7.2<br>method C |
| 6 | 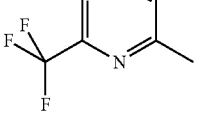 | 4-CH₃ | 3-n-C₃H₇ | HCl | 161-163° C. | MH+ 420<br>RT. 7.6<br>method B |
| 7 | 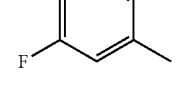 | 4-OCH₃ | 3-n-C₃H₇ | HCl | 174-177° C. | MH+ 385<br>RT. 6.7<br>method D |
| 8 | 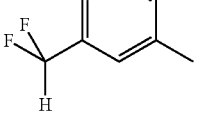 | 4-CH₃ | 3-n-C₃H₇ | HCl | 182-185° C. | MH+ 401<br>RT 10.2<br>method D |

TABLE-continued

[Structure: R1-A(aryl)-N(piperazine)N-CH2CH2-phenyl(R2)-CH2CH2-R3]

| No. | R1/A | R2 | R3 | Salt | m.p. °C. | M + H+ |
|---|---|---|---|---|---|---|
| 9 | phenyl | 4-CH₃ | 3-n-C₃H₇ | HCl | 200-202° C. | MH+ 351 RT. 6.9 method B |
| 10 | 3-methoxyphenyl | 4-CH₃ | 3-n-C₃H₇ | HCl | 199-201° C. | MH+ 381 RT 7.1 method B |
| 11 | 3-CF₃-phenyl | 4-CH₃ | isobutyl | HCl | 149° C. | MH+ 433 RT 10.2 method B |
| 12 | 3-CHF₂-phenyl | 4-OCH₃ | 3-n-C₃H₇ | HCl | 125-128° C. | MH+ 417 RT. 6.9 method D |
| 13 | 3-CF₃-phenyl | 4-OCH₃ | 3-n-C₅H₁₁ | HCl | 214° C. | MH+ 463 RT. 10.3 method A |
| 14 | 3-CF₃-phenyl | 4-CH₃ | 3-n-C₄H₉ | HCl | 187° C. | MH+ 433 RT. 7.2 method B |
| 15 | 3-CF₃-phenyl | 4-OCH₃ | 3-CH₃ | HCl | 184-185° C. | MH+ 407 RT. 6.1 method C |
| 16 | phenyl | 4-OCH₃ | 3-n-C₃H₇ | HCl | 171-173° C. | MH+ 367 RT 6.5 method B |
| 17 | 4-Cl-phenyl | 4-CH₃ | 3-n-C₃H₇ | HCl | 203° C. | MH+ 385 RT 10.9 method A |
| 18 | 6-Cl-pyridin-2-yl | 4-CH₃ | 3-n-C₃H₇ | HCl | 180-181° C. | MH+ 386 RT 10.6 method B |

TABLE-continued

Structure: R1-A(phenyl)-N(piperazine)N-CH2CH2-phenyl(R2, R3)

| No. | R1/A | R2 | R3 | Salt | m.p. °C. | M + H+ |
|---|---|---|---|---|---|---|
| 19 | 3-CF3-phenyl | 4-CH3 | 3-n-C5H11 | benzenesulfonic acid | 165° C. | MH+ 419 RT 7.2 method B |
| 20 | 3-CF3-phenyl | 4-CH3 | 3-n-C5H11 | naphthalene-2-sulfonic acid | 160-164° C. | MH+ 419 RT 7.2 method B |
| 21 | 3-CF3-phenyl | 4-CH3 | 3-n-C5H11 | p-toluenesulfonic acid | 163-165° C. | MH+ 419 RT 7.1 method B |
| 22 | 3-CF3-phenyl | 4-CH3 | 3-n-C5H11 | naphthalene-1,5-disulfonic acid 0.5 | 283-285° C. | MH+ 419 RT 7.5 method B |
| 23 | 4-F-phenyl | 4-CH3 | 3-n-C5H11 | 2*HCl | >201 | MH+ 369 RT 7.3 method G |
| 24 | 4-OMe-phenyl | 4-CH3 | 3-n-C5H11 | — | 68-70 | MH+ 381 RT 6.3 method F |
| 25 | 5-Br-pyridin-2-yl | 4-CH3 | 3-n-C5H11 | 2*HCl | 190-192 | MH+ 430 RT 6.5 method F |
| 26 | 5-CF3-pyridin-2-yl | 4-CH3 | 3-n-C5H11 | 2*HCl | >212 | MH+ 420 RT 7.6 method G |
| 27 | 4-tBu-phenyl | 4-CH3 | 3-n-C5H11 | HCl | 193-195 | MH+ 407 RT 8.3 method G |

TABLE-continued

| No. | R1-A | R2 | R3 | Salt | m.p. °C. | M + H+ |
|---|---|---|---|---|---|---|
| 28 | 4-(ethoxy)-phenyl (para-CH3, ethoxy linker) | 4-CH3 | 3-n-C5H11 | 2*HCl | 228-230 | MH+ 395 RT 7.38 method G |
| 29 | 3,5-dimethylphenyl | 4-CH3 | 3-n-C5H11 | 2*HCl | 226-228 | MH+ 365 RT 7.1 method G |
| 30 | 6-methylpyridin-2-yl | 4-CH3 | 3-n-C5H11 | 2*HCl | 183-185 | MH+ 352 RT 5.5 method E |
| 31 | 6-bromo-2-methylpyridin-... | 4-CH3 | 3-n-C5H11 | HCl | 185-187 | MH+ 430 RT 6.5 method G |
| 32 | 2-chloro-6-methylphenyl | 4-CH3 | 3-n-C5H11 | HCl | 200-202 | MH+ 385 RT 7.1 method E |
| 33 | 2,3-dimethylphenyl | 4-CH3 | 3-n-C5H11 | HCl | 220-222 | MH+ 365 RT 7.6 method E |
| 34 | 3-(trifluoromethoxy)phenyl | 4-CH3 | 3-n-C5H11 | HCl | 197-200 | MH+ 435 RT 7.8 method E |
| 35 | 5-chloro-2-methylpyridin-... | 4-CH3 | 3-n-C5H11 | HCl | 199-201 | MH+ 386 RT 7.8 method E |
| 36 | 3-(trifluoromethyl)phenyl | 4-CH$_3$ | 3-n-C$_3$H$_7$ | oxalate | 193-194 | MH+ 419 RT 6.7 method E |
| 37 | 3-(trifluoromethyl)phenyl | 4-CH$_3$ | 3-n-C$_3$H$_7$ | fumarate | 140 | MH+ 419 RT 6.9 method E |

TABLE-continued

| No. | R1-A | R2 | R3 | Salt | m.p. °C. | M + H+ |
|---|---|---|---|---|---|---|
| 38 | 3-(F₂FC)-phenyl (3,3-difluoro... methyl) | 4-CH₃ | 3-n-C₃H₇ | succinate | 95-96 | MH+ 419 RT 6.6 method E |
| 39 | 3-(F₂FC)-phenyl | 4-CH₃ | 3-n-C₃H₇ | dihippurate | 91-92 | MH+ 419 RT 6.7 method E |

The compounds of the invention have advantageous properties as TNF-α inhibitors.

These properties were demonstrated using a test aimed at measuring the effect of molecules on the synthesis of TNF-α induced in Balb/c mice by a lipopolysaccharide (LPS) from *Escherichia coli* (055:B5, Sigma, St Louis, Mo.).

The test products are administered orally to groups of five 7- to 8-week-old female Balb/c mice (Charles River, France). One hour later, LPS is administered intravenously (10 μg/mouse). The blood of each animal is collected 1.5 hours after the LPS administration. The samples are centrifuged, and the plasma is recovered and frozen at −80° C. The TNF-α is measured using commercial kits (R & D, Abingdon, UK).

In this test, compound 38 was shown to be very active, inhibiting the synthesis of TNF-α even at very low doses, IC50=0.1 mg/Kg These properties were also demonstrated using a test aimed at measuring the effect of molecules on the synthesis of TNF-α induced in Sprague-Dawley rats by a lipopolysaccharide (LPS) from *Escherichia coli* (055:B5, Sigma, St Louis, Mo.).

The test products are administered orally to groups of ten male Sprague-Dawley rats weighing about 200 grams. Two hours later, LPS is administered intravenously (0.1 mg/Kg). The blood of each animal is collected 1.5 hours after the LPS administration. The samples are centrifuged, and the serum is recovered and frozen at −80° C. The TNF-α is measured using commercial kits (RPN 2744 Amersham, UK).

In this test, the compounds were shown to be very active, inhibiting the synthesis of TNF-α even at very low doses, IC50=from 0.3 to 1 mg/Kg, especially with an IC50=0.3 mg/Kg for compound 1 and an IC50=1 mg/Kg for compounds 4 and 8.

The compounds of the invention are tested in a model of joint inflammation.

The compound (1 ng/joint as a suspension in 10 μL of a solution of 2% PVP (polyvinylpyrrolidone)/1% lutrol F68/ 0.9% NaCl) according to the invention is injected one hour before the first injection of Zymosan® (see below) into the joint of a hamster.

Induction of a knee joint inflammation: Under light anaesthesia using isofluran, a suspension of Zymosan® at a dose of 100 μg in 10 μL of saline solution is injected into the knee joint of a male hamster. Zymosan® is a yeast extract which produces a strong dose-dependent inflammation when subcutaneously injected. Under the experimental conditions described herein (injection into the knee joint), it induces a hyperalgesia lasting for a week. In order to extend this period, 3 consecutive injections of Zymosan® were applied. The lag time to paw withdrawal, following exposure of the plantar skin to a defined heat stimulus, is measured using apparatus (Plantar Test Ugo Basile Biological Research Apparatus, Comerio, Italy) comprising a mini-camera to ensure the correct positioning of the infrared ray below the hind leg of interest.

Measurement of Secondary Hyperalgesia:

The timer, which measures the length of time the infrared light is reflected by the hind leg, is started by the investigator and stops automatically as soon as the animal shakes or pulls away its leg. The infrared light is stopped after 16 seconds by the investigator if the animal does not pull its leg away, to avoid burning injuries. The lag time to leg withdrawal in seconds is used as a measurement of pain. The measurement was performed 4 hours after the first injection of Zymosan® and during the following 3 weeks. In this test, representative compounds of the invention, and especially compound 1, show an effective reduction of pain over a 3-week period.

The compounds of the invention are also tested in a model of neuropathic pain: measurement of the anti-allodynic effect in the spare nerve injury (SNI).

In this in vivo model of mice suffering from chronic neuropathic pain, the effect on tactile allodynia, a painful sensation induced after a mechanical stimulus not normally painful, is triggered in the hind leg by surgical lesion of the great sciatic nerve. It is then determined by measuring the paw withdrawal threshold (PWT), i.e. the applied force (expressed in grams) at which the mouse withdraws its hind leg.

Tactile allodynia is determined on both hind legs, i.e. homolaterally and controlaterally to the lesion determined following surgery, with the automatic von Frey test, in which the plantar skin of the hind legs is exposed to a pressure stimulus of increasing intensity reaching 5 grams, using a discharge needle prod. The force in grams to which the animal responded by withdrawal of the hind leg (paw withdrawal threshold, PWT) is used as a measurement of tactile allodynia.

Trial groups using the compounds according to the invention and a control group of animals were used, each being composed of four male C57B6 mice. In each group, the baseline of the PWT values (BL) was determined before surgery. Under general anaesthesia and in order to induce neuropathic pain, the two major branches of the great sciatic nerve are ligated and transversely sectioned, with the sural nerve left untouched (spare nerve injury, SNI). In this model of neuropathic pain, tactile allodynia completely developed within two days of the transverse section of the nerve in the hind leg homolaterally to the lesion and remains stable in the control group during the observation period of the experiment.

7 days after surgery, just before the administration of the compound, i.e. at 0 h, and in all the groups, the PWT values were determined for the homolateral hind leg (injured) and the controlateral hind leg (non-injured). The compounds according to the invention or the vehicle were administered to the animals by injection into the tail vein (i.v.). In the trial groups, the mice received 0.1 ml/10 g of a solution of the test compounds in the vehicle (1/1/18 Ethanol/Cremophor/Phosphate Buffered Saline) at a dose of 1 mg/kg. In the control group, the mice analogously received 0.1 ml/10 g of vehicle. 1 h, 2 h, 4 h and 6 h after administration, the PWT values were determined.

For the statistical analysis, the measured PWT values were analysed by 1-way ANOVA and Bonferroni Multiple Comparison. At the evaluated dose (1 mg/kg i.v.), a statistically significant reduction of pain (by measurement of the anti-allodynic effect) was observed for Example 1 from 1 h to 6 h.

By virtue of this activity, the compounds of formula (I) and their salts may be used for treating diseases associated with immune and inflammatory disorders or as analgesics for treating pain.

In particular, the compounds of formula (I) may be used for treating atherosclerosis, autoimmune diseases, diseases that result in neuron demyelination (such as multiple sclerosis), asthma, pain or inflammation of the joints, more particularly of the shoulder, the knee, the fingers, etc., rheumatoid arthritis and its articular pains, osteoarthritis and its articular pains, and also other inflammatory pains of the joints, or other inflammatory pains (e.g. hygroma, tendinitis, etc.), fibrotic diseases, pulmonary idiopathic fibrosis, mucoviscidosis, glomerulonephritis, rheumatoid spondylitis, gout, bone and cartilage resorption, osteoporosis, Paget's disease, multiple myeloma, uveoretinitis, septic shock, septicaemia, endotoxic shocks, graft-versus-host disease, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, systemic lupus erythematosus, haemodynamic shocks, ischaemic pathologies (myocardial infarction, myocardial ischemia, coronary vasospasm, angina, heart failure, heart attack), post-ischaemic reperfusion lesions, malaria, mycobacterial infections, meningitis, leprosy, viral infections (HIV, cytomegalovirus, herpesvirus), AIDS-related opportunistic infections, tuberculosis, psoriasis, atopic and contact dermatitis, diabetes, cachexia, cancer, and radiation-induced damage.

According to one of its aspects, the present invention relates to a compound according to the invention, or a pharmaceutically acceptable salt of the said compound, for treating the abovementioned diseases.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, intraarticular, topical, local, intratracheal, intranasal, transdermal or rectal administration, the active principle of formula (I) above, or the salt thereof, may be administered in unit administration form, as a mixture with standard pharmaceutical excipients, to man and animals for the prophylaxis or treatment of the above complaints or diseases.

The appropriate unit forms of administration include oral forms such as tablets, soft or hard gel capsules, powders, granules and oral solutions or suspensions, sublingual, buccal, intratracheal, intraocular, intranasal or inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit form of administration of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

Via the oral route, the dose of active principle given per day can reach 0.01 to 100 mg/kg, and preferentially from 0.02 to 50 mg/kg, in one or more dosage intakes.

By way of example, a unit form of administration of a compound according to the invention in the form of an intraarticular solution or suspension may comprise the following components:

| Compound according to the invention | |
|---|---|
| Polyvinylpyrrolidone (PVP) K17 | 2% |
| Lutrol F68 | 1% |
| NaCl | 0.9% |

Via the intraarticular route, the dose of active principle given can reach 0.01 to 40 mg/kg per joint, the frequency between injections preferentially being of at least one month.

As a further example, a unit form of administration of a compound according to the invention in the form of an intraarticular solution or suspension may comprise the following components:

| | |
|---|---|
| Compound according to the invention | 48 mg |
| Polyvinylpyrrolidone (PVP) | 20 mg |

| | |
|---|---|
| Poloxamer 188 | 10 mg |
| NaCl | 9 mg |
| 0.1N NaOH/0.1N HCl | qs pH adjusted to 6.8-7.4 |
| Water for injection | 1000 mg |

Via the intraarticular route, the dose of active principle given can reach 4 ng to 96 mg per joint, the frequency between injections preferentially being of at least one month.

There may be particular cases in which higher or lower dosages are appropriate; such dosages are not outside the context of the invention. According to the usual practice, the dosage that is appropriate for each patient is determined by the doctor according to the mode of administration and the weight and response of the said patient.

According to another one of its aspects, the present invention also relates to a method for treating the abovementioned pathologies, comprising the administration, to a patient, of an effective dose of a compound according to the invention, or a pharmaceutically acceptable salt thereof.

According to another one of its aspects, the invention relates to a method for treating diseases associated with immune and inflammatory disorders, and also for treating pain, in particular atherosclerosis, autoimmune diseases, diseases that result in neuron demyelination (such as multiple sclerosis), asthma, rheumatoid arthritis and its articular pains, osteoarthritis and its articular pains, and also other inflammatory pains of the joints, or other inflammatory pains (e.g. hygroma, tendinitis, etc.), fibrotic diseases, pulmonary idiopathic fibrosis, mucoviscidosis, glomerulonephritis, rheumatoid spondylitis, gout, bone and cartilage resorption, osteoporosis, Paget's disease, multiple myeloma, uveoretinitis, septic shock, septicaemia, endotoxic shocks, graft-versus-host disease, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, systemic lupus erythematosus, hemodynamic shocks, ischemic pathologies (myocardial infarction, myocardial ischaemia, coronary vasospasm, angina, heart failure, heart attack), post-ischaemic reperfusion lesions, malaria, mycobacterial infections, meningitis, leprosy, viral infections (HIV, cytomegalovirus, herpesvirus), AIDS-related opportunistic infections, tuberculosis, psoriasis, atopic and contact dermatitis, diabetes, cachexia, cancer, and radiation-induced damage, comprising the administration of a compound of formula (I) or a pharmaceutically acceptable salt thereof, alone or in combination with other active principles.

According to another one of its aspects, the invention relates to a method for treating pain or inflammations of the joints, more particularly those of the shoulder, the knee or the fingers, comprising the administration of a compound of formula (I) or a pharmaceutically acceptable salt thereof, alone or in combination with other active principles. The invention also relates to a treatment method as mentioned above, in which the administration of a compound of formula (I) or a pharmaceutically acceptable salt thereof, alone or in combination with other active principles, is performed via intraarticular injection.

According to another one of its aspects, the invention relates to the use of a compound of formula (I) or a pharmaceutically acceptable salt thereof for the preparation of a medicament for treating pain or inflammations of the joints, or, more particularly, the use of a compound of formula (I) or a pharmaceutically acceptable salt thereof, characterized in that the medicament is injected into the joint.

According to another one of its aspects, the invention relates to a compound of formula (I) or a pharmaceutically acceptable salt thereof for treating pain or inflammations of the joints, or, more particularly, the treatment characterized in that the medicament is injected into the joint.

What is claimed is:

1. A compound of formula (I):

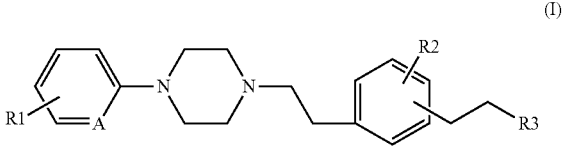

in which:
R1 and R2 represent, independently of each other, a hydrogen atom, a halogen atom, a (C1-C5)alkyl group, a (C1-C5)haloalkyl group, a (C1-C2)perfluoroalkyl group, a (C1-C5)alkoxy group or a (C1-C2)perfluoroalkoxy group;
R3 represents a (C1-C5)alkyl group; and
A represents =CH— or =N—;
in the form of the base or an acid-addition salt.

2. A compound according to claim 1, wherein
R1 represents a (C1-C5)haloalkyl group or a (C1-C2)perfluoroalkyl group; in the form of the base or an acid-addition salt.

3. A compound according to claim 2, wherein
R1 represents a (C1-C5)fluoroalkyl group; in the form of the base or an acid-addition salt.

4. A compound according to claim 1, wherein
R2 represents a hydrogen atom or a (C1-C5)alkyl group; in the form of the base or an acid-addition salt.

5. A compound according to claim 1, wherein the piperazine group is linked via the ethyl group to position 3 and R3 is linked to position 1 on the phenyl group:

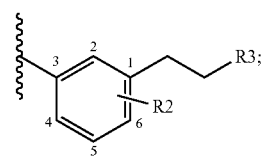

in the form of the base or an acid-addition salt.

6. A compound according to claim 1, wherein
R1 represents a (C1-C2)perfluoroalkyl group; in the form of the base or an acid-addition salt.

7. A compound according to claim 1, wherein
R2 represents a hydrogen atom or a (C1-C3)alkyl group, in the form of the base or an acid-addition salt.

8. A compound according claim 1, wherein the compound is 1-[2-(4-methyl-3-pentylphenyl)ethyl]-4-(3-trifluoromethylphenyl)piperazine; in the form of the base or an acid-addition salt.

9. A compound according to claim 1, chosen from:
compound 1: 1-(3-trifluoromethylphenyl)-4-[2-(4-methyl-3-pentylphenyl)ethyl]-piperazine hemipamoate;
compound 1 bis: 1-(3-trifluoromethylphenyl)-4-[2-(4-methyl-3-pentylphenyl)ethyl]-piperazine hemipamoate as a mixture with 0.5 mol of free pamoic acid;
compound 2: 1-(3-trifluoromethylphenyl)-4-[2-(4-methoxy-3-pentylphenyl)ethyl]-piperazine hydrochloride;

compound 3: 1-(3-trifluoromethylphenyl)-4-[2-(4-methyl-3-propylphenyl)ethyl]-piperazine hydrochloride;
compound 4: 1-(3-fluorophenyl)-4-[2-(4-methyl-3-pentylphenyl)ethyl]piperazine hydrochloride;
compound 5: 1-(3-trifluoromethylphenyl)-4-[2-(4-methyl-3-heptylphenyl)ethyl]-piperazine hydrochloride;
compound 6: 1-(6-trifluoromethylpyrid-2-yl)-4-[2-(4-methyl-3-pentylphenyl)ethyl]-piperazine hydrochloride;
compound 7: 1-(3-fluorophenyl)-4-[2-(4-methoxy-3-pentylphenyl)ethyl]piperazine hydrochloride;
compound 8: 1-(3-difluoromethylphenyl)-4-[2-(4-methyl-3-pentylphenyl)ethyl]-piperazine hydrochloride;
compound 9: 1-(phenyl)-4-[2-(4-methyl-3-pentylphenyl)ethyl]piperazine hydrochloride;
compound 10: 1-(3-methoxypheny)-4-[2-(4-methyl-3-pentylphenyl)ethyl]piperazine hydrochloride;
compound 11: 1-(3-trifluoromethylpheny)-4-[2-(4-methyl-3-(2-methylbutyl)-phenyl)ethyl]piperazine hydrochloride;
compound 12: 1-(3-difluoromethylphenyl)-4-[2-(4-methoxy-3-pentylphenyl)ethyl]-piperazine hydrochloride;
compound 13.: 1-(3-trifluoromethylphenyl)-4-[2-(4-methoxy-3-heptylpheny)pethyl]-piperazine hydrochloride;
compound 14: 1-(3-trifluoromethylphenyl)-4-[2-(4-methyl-3-hexylphenyl)ethyl]-piperazine hydrochloride;
compound 15: 1-(3-trifluoromethylphenyl)-4-[2-(4-methoxy-3-propylpheny)ethyl]-piperazine hydrochloride;
compound 16: 1-(phenyl)-4-[2-(4-methoxy-3-pentylphenyl)ethyl]piperazine hydrochloride;
compound 17: 1-(4-chloropheny)-4-[2-(4-methyl-3-pentylphenyl)ethyl]piperazine hydrochloride;
compound 18: 1-(3-trifluoromethylphenyl)-4-[2-(4-methyl-3-pentylphenyl)ethyl]-piperazine hydrochloride;
compound 19: 1-(3-trifluoromethylphenyl)-4-[2-(4-methyl-3-pentylphenyl)ethyl]-piperazine benzenesulfonate;
compound 20: 1-(3-trifluoromethylphenyl)-4-[2-(4-methyl-3-pentylphenyl)ethyl]-piperazine 2-naphthalenesulfonate;
compound 21: 1-(3-trifluoromethylphenyl)-4-[2-(4-methyl-3-pentylphenyl)ethyl]-piperazine p-tolylsulfonate;
compound 22: 1-(3-trifluoromethylphenyl)-4-[2-(4-methyl-3-pentylphenyl)ethyl]-piperazine hemi-2,5-naphthalenedisulfonate;
compound 23: 1-(4-fluorophenyl)-4-[2-(4-methyl-3-pentylphenyl)ethyl]piperazine dihydrochloride;
compound 24: 1-(4-methoxyphenyl)-4-[2-(4-methyl-3-pentylphenyl)ethyl]piper-azine (base);
compound 25: 1-(5-bromopyrid-2-yl)-4-[2-(4-methyl-3-pentylphenyl)ethyl]piper-azine dihydrochloride;
compound 26: 1-[2-(4-methyl-3-pentylphenyl)ethyl]-4-(5-trifluoromethylpyrid-2-yl)piperazine dihydrochloride;
compound 27: 1-(4-tert-butylphenyl)-4-[2-(4-methyl-3-pentylphenyl)ethyl]piper-azine hydrochloride;
compound 28: 1-(4-ethoxyphenyl)-4-[2-(4-methyl-3-pentylpheny)ethyl]piperazine dihydrochloride;
compound 29: 1-[2-(4-methyl-3-pentylphenyl)ethyl]-4-m-tolylpiperazine dihydrochloride;
compound 30: 1-[2-(4-methyl-3-pentylphenyl)ethyl]-4-pyrid-2-ylpiperazine dihydrochloride;
compound 31: 1-(6-bromopyrid-2-yl)-4-[2-(4-methyl-3-pentylphenyl)ethyl]piper-azine hydrochloride;
compound 32: 1-(2-chlorophenyl)-4-[2-(4-methyl-3-pentylphenyl)ethyl]piperazine hydrochloride;
compound 33: 1-(2-methylphenyl)-4-[2-(4-methyl-3-pentylphenyl)ethyl]piperazine hydrochloride;
compound 34: 1-(3-trifluoromethoxylphenyl)-4-[2-(4-methyl-3-pentylphenyl)ethyl]-piperazine hydrochloride;
compound 35: 1-(5-chloropyrid-2-yl)-4-[2-(4-methyl-3-pentylphenyl)ethyl]piper-azine hydrochloride;
compound 36: 1-(3-trifluoromethylphenyl)-4-[2-(4-methyl-3-pentylphenyl)ethyl]-piperazine oxalate;
compound 37: 1-(3-trifluoromethylphenyl)-4-[2-(4-methyl-3-pentylphenyl)ethyl]-piperazine fumarate;
compound 38: 1-(3-trifluoromethylphenyl)-4-[2-(4-methyl-3-pentylphenyl)ethyl]-piperazine succinate; or
compound 39: 1-(3-trifluoromethylphenyl)-4-[2-(4-methyl-3-pentylphenyl)ethyl]-piperazine dihippurate.

10. A process for preparing a compound according to claim 1, comprising the step of condensing a compound of formula (II):

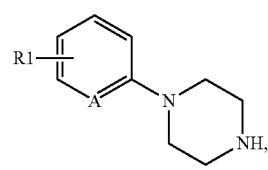

in which R1 and A are as defined in claim 1, with a compound of formula (III):

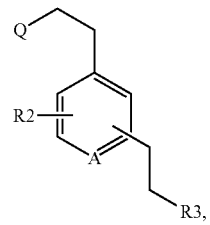

in which R2 and R3 are as defined in claim 1, and Q represents a leaving group, and optionally converting it into a salt thereof.

11. A pharmaceutical composition comprising a compound of formula (I) according to claim 1, or a pharmaceutically acceptable salt thereof, and at least one pharmaceutically acceptable excipient.

12. A method for treating pain or inflammation of joints, the method comprising administering to a patient in need thereof an effective dose of a compound as claimed in claim 1.

13. The method of claim 12 wherein the compound is injected into the joints.

* * * * *